United States Patent
DeLuca et al.

(10) Patent No.: US 8,399,438 B2
(45) Date of Patent: *Mar. 19, 2013

(54) 2α-METHYL-19-NOR-1α-HYDROXY-HOMOPREGNACALCIFEROL AND ITS USES

(75) Inventors: Hector F. DeLuca, Deerfield, WI (US); Rafal R. Sicinski, Warsaw (PL); Lori A. Plum, Arena, WI (US); Margaret Clagett-Dame, Deerfield, WI (US); Sumithra Gowlugari, Fremont, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 503 days.

This patent is subject to a terminal disclaimer.

(21) Appl. No.: 11/283,261

(22) Filed: Nov. 18, 2005

(65) Prior Publication Data

US 2006/0148759 A1    Jul. 6, 2006

Related U.S. Application Data

(60) Provisional application No. 60/630,181, filed on Nov. 22, 2004.

(51) Int. Cl.
*A61K 31/59* (2006.01)
*C07C 401/00* (2006.01)

(52) U.S. Cl. ........................................ 514/167; 552/653
(58) Field of Classification Search ................... 552/653; 514/167
See application file for complete search history.

(56) References Cited

U.S. PATENT DOCUMENTS

| | | | |
|---|---|---|---|
| 4,666,634 A | 5/1987 | Miyamoto et al. | |
| 5,536,713 A | 7/1996 | DeLuca et al. | |
| 5,843,928 A | 12/1998 | DeLuca et al. | |
| 5,905,074 A * | 5/1999 | Schneider | 514/167 |
| 5,945,410 A | 8/1999 | DeLuca et al. | |
| 6,281,249 B1 * | 8/2001 | DeLuca et al. | 514/675 |
| 6,566,352 B1 | 5/2003 | DeLuca et al. | |
| 6,579,861 B2 | 6/2003 | DeLuca et al. | |
| 6,627,622 B2 | 9/2003 | DeLuca et al. | |
| 6,992,074 B2 * | 1/2006 | DeLuca et al. | 514/167 |
| 2009/0221529 A1 * | 9/2009 | Brard et al. | 514/80 |

FOREIGN PATENT DOCUMENTS

WO   WO 2005/051323   6/2005

OTHER PUBLICATIONS

Choi et al, "Interaction between Vitamin D Receptor and Vitamin D Ligands: Two-Dimensional Alanine Scanning Mutational Analysis," Chemistry & Biology, vol. 10, pp. 261-270, (2003).
DeLuca et al, "Therapeutic Potential of the 2-Alkyl and 2-Alkylidene-19-Nor-(20S)-Modified Analogs of 1α,25-Dihydroxyvitamin $D_3$," Journal of Steroid Biochemistry & Molecular Biology, 89-90, pp. 67-73, (2004).

* cited by examiner

*Primary Examiner* — Sabiha N Qazi
(74) *Attorney, Agent, or Firm* — Andrus, Sceales, Starke & Sawall, LLP (57) ABSTRACT

This invention discloses 2α-methyl-19-nor-vitamin D analogs, and specifically 2α-methyl-19-nor-1α-hydroxy-homopregnacalciferol and pharmaceutical uses therefor. This compound exhibits pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also has little, if any, calcemic activity and therefore may be used to treat autoimmune disorders or inflammatory diseases in humans as well as renal osteodystrophy. This compound may also be used for the treatment or prevention of obesity.

67 Claims, 6 Drawing Sheets

2α-METHYL-19-NOR-1α-HYDROXY-HOMOPREGNACALCIFEROL AND ITS USES

CROSS REFERENCE TO RELATED APPLICATION

This application claims priority to U.S. Provisional Application No. 60/630,181, filed Nov. 22, 2004.

BACKGROUND OF THE INVENTION

This invention relates to vitamin D compounds, and more particularly to 2α-methyl-19-nor-1α-hydroxy-homopregnacalciferol and its pharmaceutical uses.

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566, 352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

SUMMARY OF THE INVENTION

The present invention is directed toward 2α-methyl-19-nor-vitamin D analogs, and more specifically toward 2α-methyl-19-nor-1α-hydroxy-homopregnacalciferol, their biological activity, and various pharmaceutical uses for these compounds. These new 1α-hydroxylated vitamin D compounds not known heretofore are the 19-nor-vitamin D analogs having a methyl group at the 2-position, and iso-propyl substituent at the 17-position (C-17).

Structurally these 2α-methyl-19-nor-vitamin D analogs are characterized by the general formula I shown below:

I where $X_1$ and $X_2$, which may be the same or different, are each selected from hydrogen or a hydroxy-protecting group. The preferred analog is 2α-methyl-19-nor-1α-hydroxy-homopregnacalciferol which has the following formula Ia:

Ia

The above compounds I, and particularly Ia, exhibit a desired, and highly advantageous, pattern of biological activity. These compounds are characterized by relatively high binding to vitamin D receptors, but very low intestinal calcium transport activity, as compared to that of 1α,25-dihydroxyvitamin $D_3$, and have very low ability to mobilize calcium from bone, as compared to 1α,25-dihydroxyvitamin $D_3$. Hence, these compounds can be characterized as having little, if any, calcemic activity. It is undesirable to raise serum calcium to supraphysiologic levels when suppressing the pre-proparathyroid hormone gene (Darwish & DeLuca, Arch. Biochem. Biophys. 365, 123-130, 1999) and parathyroid gland proliferation. These analogs having little or no calcemic activity while very active on differentiation are expected to be useful as a therapy for suppression of secondary hyperparathyroidism of renal osteodystrophy.

The compounds I, and particularly Ia, of the invention have also been discovered to be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the invention.

The above compounds I, and particularly Ia, are also characterized by relatively high cell differentiation activity. Thus, these compounds also provide a therapeutic agent for the treatment of psoriasis, or as an anti-cancer agent, especially against leukemia, colon cancer, breast cancer, skin cancer and prostate cancer. In addition, due to their relatively high cell differentiation activity, these compounds provide a therapeutic agent for the treatment of various skin conditions including wrinkles, lack of adequate dermal hydration, i.e. dry skin, lack of adequate skin firmness, i.e. slack skin, and insufficient sebum secretion. Use of these compounds thus not only results in moisturizing of skin but also improves the barrier function of skin.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of one or more of the compounds or the pharmaceutical compositions to the subject inhibits adipocyte differentiation, inhibits gene transcription, and/or reduces body fat in the animal subject.

One or more of the compounds may be present in a composition to treat the above-noted diseases and disorders in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually or parenterally in dosages of from about 0.01 μg/day to about 1000 μg/day, preferably from about 0.1 μg/day to about 500 μg/day.

BRIEF DESCRIPTION OF THE DRAWINGS

FIGS. 1-6 illustrate various biological activities of 2α-methyl-19-nor-1α-hydroxy-homopregnacalciferol, hereinafter referred to as "2α-methylP," as compared to the native hormone 1α,25-dihydroxyvitamin $D_3$, hereinafter "1,25(OH)$_2$ $D_3$."

DETAILED DESCRIPTION OF THE INVENTION

2α-methyl-19-nor-1α-hydroxy-homopregnacalciferol (referred to herein as 2α-methylP), a 19-nor vitamin D analog which is characterized by the presence of a methyl substituent at the carbon 2 (C-2) and an iso-propyl substituent at the carbon 17 (C-17), was synthesized and tested. Such vitamin D analog seemed an interesting target because the relatively small methyl group at the C-2 position should not interfere with binding to the vitamin D receptor. Structurally, this 19-nor analog is characterized by the general formula Ia previously illustrated herein, and its pro-drug (in protected hydroxy form) is illustrated by general formula I.

The preparation of 2α-methyl-19-nor-1α-hydroxy-homopregnacalciferol analogs having the structure I can be accomplished by a common general method, i.e. the selective homogeneous catalytic hydrogenation of the exomethylene unit at carbon 2 in the 2-methylene-19-nor-1α-hydroxy-homo-pregnacalciferol compounds of the general formula II performed efficiently in the presence of tris(triphenylphosphine)rhodium(I) chloride [Wilkinson's catalyst, (Ph$_3$P)$_3$RhCl]. Such reduction conditions allowed to reduce only C(2)=CH$_2$ unit leaving C(5)-C(8) butadiene moiety unaffected. The isolated material is an epimeric mixture (ca. 1:1) of 2-methyl-19-nor-vitamins I and III differing in configuration at C-2. The mixture can be used without separation or, if desired, the individual 2α-(formula I) and 2β-(formula III) isomers can be separated by an efficient HPLC system.

II

In the structures I, II and III, substituents $X_1$ and $X_2$ represent the groups defined above.

2-methylene-19-nor-homopregnacalciferol analogs of the general structure II are known, or can be prepared by known methods.

The overall process of the synthesis of compounds I, II and III is illustrated and described more completely in U.S. Pat. No. 5,843,928 entitled "2-Alkylidene-19-Nor-Vitamin D Compounds" the specification of which is specifically incorporated herein by reference.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

More specifically, reference should be made to the following illustrative example and description as well as to Scheme 1 herein for a detailed illustration of the preparation of compound 2α-methylP.

In this example specific products identified by Arabic numerals (1, 2, 3) refer to the specific structures so identified in the Scheme I.

EXAMPLE

Chemistry. Ultraviolet (UV) absorption spectra were recorded with a Hitachi Model 60-100 UV-vis spectrometer in the solvent noted. $^1$H nuclear magnetic resonance (NMR) spectra were recorded at 500 MHz with a Bruker AM-500 FT spectrometer in deuteriochloroform. Chemical shifts (δ) are reported downfield from internal Me$_4$Si (δ 0.00). Mass spectra were recorded at 70 eV on a Kratos DS-50 TC instrument equipped with a Kratos MS-55 data system. Samples were introduced into the ion source maintained at 120-250° C. via a direct insertion probe. High-performance liquid chromatography (HPLC) was performed on a Waters Associates liquid chromatograph equipped with a Model 6000A solvent delivery system, a Model 6 UK Universal injector, a Model 486 tunable absorbance detector, and a differential R 401 refractometer.

Example 1

Hydrogenation of 2-methylene-19-nor-1α-hydroxy-homopregnacalciferol (1)

Tris(triphenylphosphine)rhodium (I) chloride (32.0 mg, 34.6 μmol) was added to dry benzene (35 mL) presaturated with hydrogen (for 20 min). The mixture was stirred at room temperature until a homogeneous solution was formed (ca. 70 min). A solution of vitamin 1 (11 mg, 33.3 μmol) in dry benzene (6 mL) was then added and the reaction was allowed to proceed under a continuous stream of hydrogen for 3.5 h. Benzene was removed under vacuum, the residue was redissolved in hexane/ethyl acetate (7:3) and applied on Waters silica Sep-Pak (Vac 12 cc). The crude 2-methyl vitamins (ca. 11 mg) were eluted with the same solvent system (35 mL). The combined fractions were evaporated and they were further purified by HPLC (10 mm×25 cm Zorbax-Sil column, 4 mL/min) using hexane/2-propanol (90:10) solvent system. The mixture (ca. 1:1) of both 2α- and 2β-methyl-19-norvitamins 2 and 3 (53:47 ratio; 6.37 mg, 58%) gave a single peak at R$_V$ 29 mL. Separation of both epimers was achieved by reversed-phase HPLC (6.2 mm×25 cm Zorbax-ODS column, 2 mL/min) using methanol/water (90:10) solvent system. 2β-Methyl vitamin 3 was collected at R$_V$ 17 mL and its 2α-epimer 2 at R$_V$ 19 mL.

2: UV (in EtOH) λ$_{max}$ 242.0, 250.0, 260.0 nm; $^1$H NMR (CDCl$_3$) δ 0.531 (3H, s, 18-H$_3$), 0.860 and 0.940 (3H and 3H, each d, J=6.5 Hz, 21- and 22-H$_3$), 1.134 (3H, d, J=6.8 Hz, 2α-CH$_3$), 2.13 (1H, ~t, J~11 Hz, 4β-H), 2.22 (1H, br d, J~13 Hz, 10β-H), 2.60 (1H, dd, J=12.9, 4.1 Hz, 4α-H), 2.80 (2H, m, 9β- and 10α-H), 3.61 (1H, m, w/2=23 Hz, 3αα-H), 3.96 (1H, m, w/2=14 Hz, 1β-H), 5.82 and 6.37 (1H and 1H, each d, J=11.2 Hz, 7- and 6-H); MS m/z (relative intensity) 332 (M$^+$, 100), 289 (37), 253 (21), 177 (67), 135 (76), 91 (78); exact mass calcd for C$_{22}$H$_{36}$O$_2$ 332.2715. Found 332.2712.

SCHEME I

BIOLOGICAL ACTIVITY OF 2α-METHYL-19-NOR-1α-HYDROXY-HOMOPREGNACALCIFEROL

Figure 1:
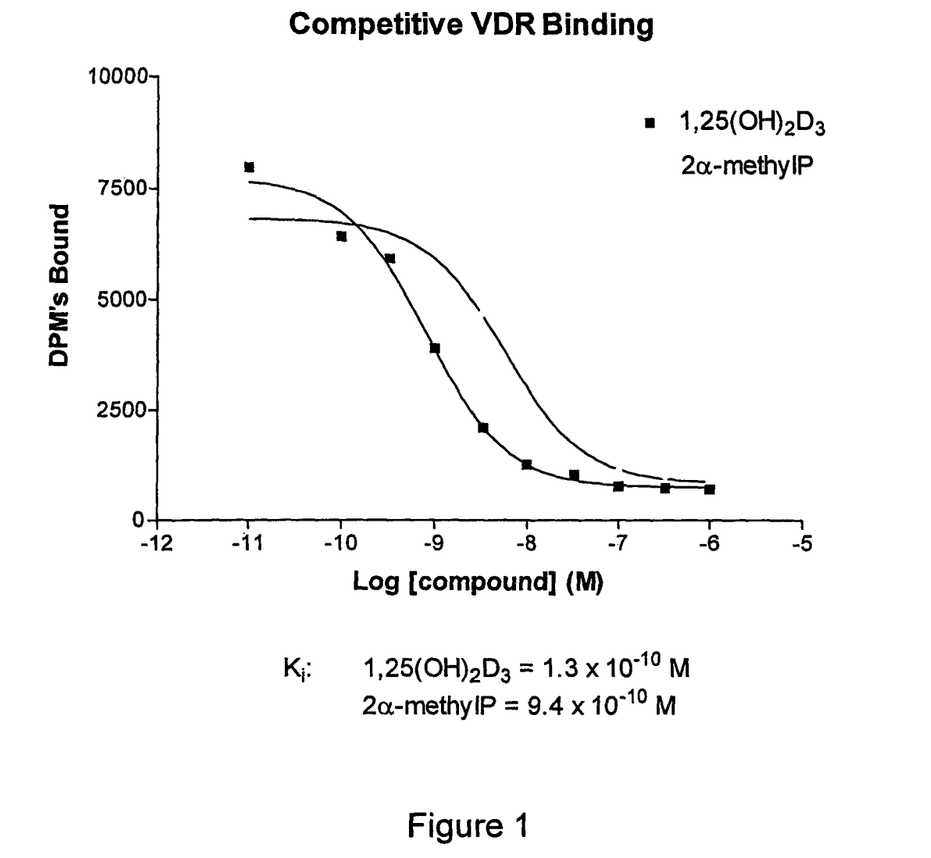
FIG. 1 is a graph illustrating the relative activity of 2α-methylP and 1,25(OH)-$_2D_3$ to compete for binding with [$^3$H]-1,25-(OH)$_2$-$D_3$ to the full-length recombinant rat vitamin D receptor.

The introduction of a methyl group to the 2-position, and the elimination of carbons 23, 24, 25, 26 and 27 in the side chain of 1α-hydroxy-19-nor-vitamin $D_3$ had little or no effect on binding to the full length recombinant rat vitamin D receptor, as compared to 1α,25-dihydroxyvitamin $D_3$. The compound 2α-methylP bound equally well to the receptor as compared to the standard 1,25-$(OH)_2D_3$ (FIG. 1). It might be expected from these results that compound 2α-methylP would have equivalent biological activity. Surprisingly, however, compound 2α-methylP is a highly selective analog with unique biological activity.

Figure 5:
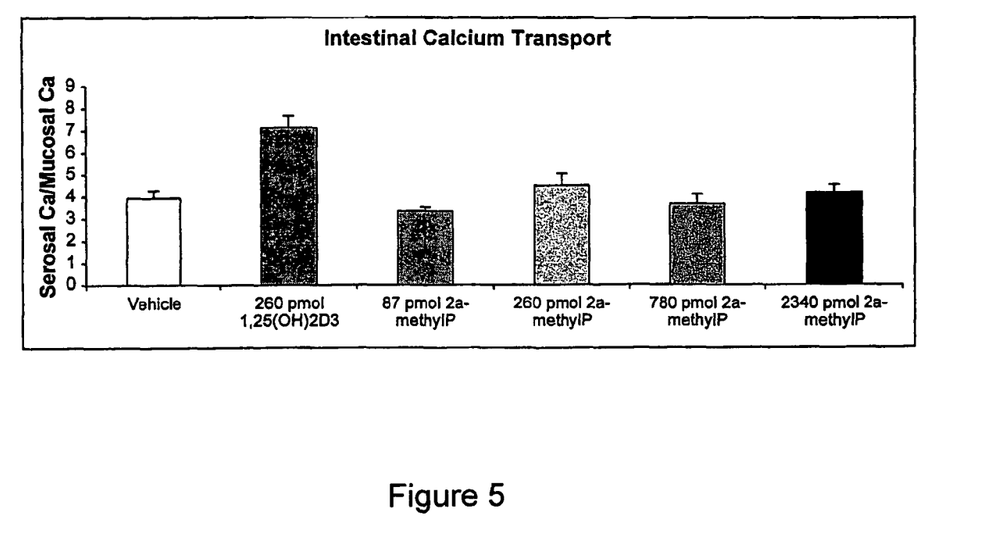
FIG. 5 is a bar graph illustrating the intestinal calcium transport activity of 1,25(OH)$_2D_3$ as compared to 2α-methylP.

FIG. 5 shows that 2α-methylP has very little activity as compared to that of 1,25-dihydroxyvitamin $D_3$ (1,25(OH)$_2D_3$), the natural hormone, in stimulating intestinal calcium transport.

Figure 4:
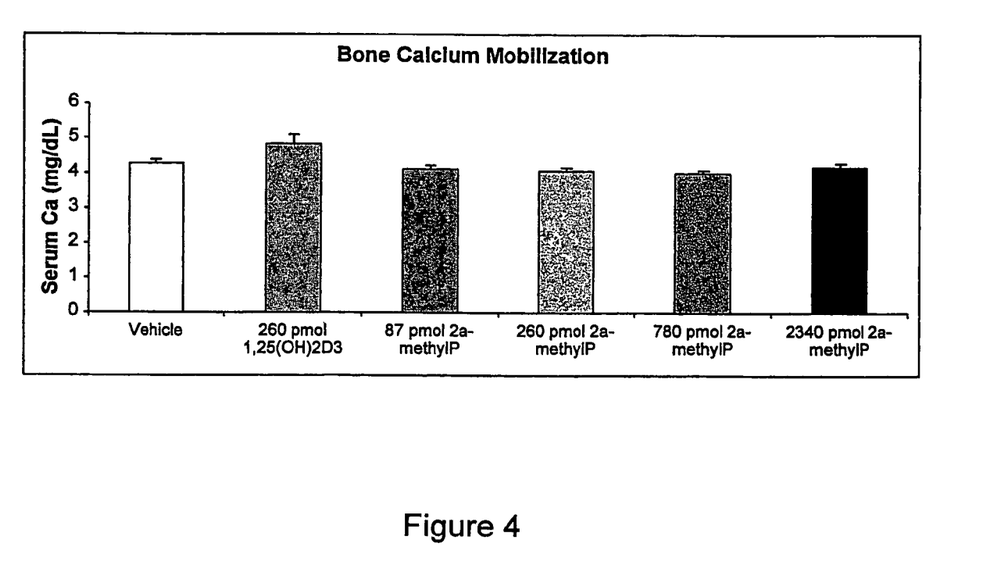
FIG. 4 is a bar graph illustrating the bone calcium mobilization activity of 1,25(OH)$_2D_3$ as compared to 2α-methylP.

FIG. 4 demonstrates that 2α-methylP has very little bone calcium mobilization activity, as compared to 1,25$(OH)_2D_3$.

FIGS. 4 and 5 thus illustrate that 2α-methylP may be characterized as having little, if any, calcemic activity.

Figure 2:
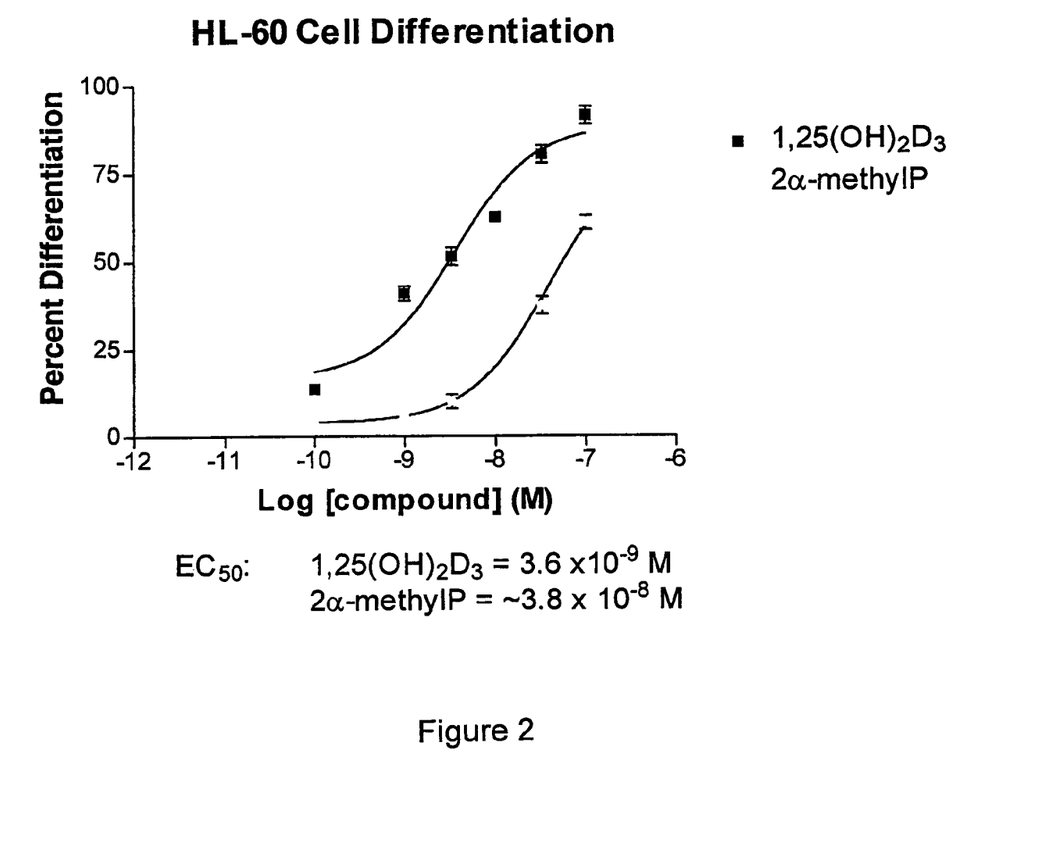
FIG. 2 is a graph illustrating the percent HL-60 cell differentiation as a function of the concentration of 2α-methylP and 1,25(OH)$_2D_3$.

FIG. 2 illustrates that 2α-methylP is almost as potent as 1,25$(OH)_2D_3$ on HL-60 cell differentiation, making it an excellent candidate for the treatment of psoriasis and cancer, especially against leukemia, colon cancer, breast cancer, skin cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 3:
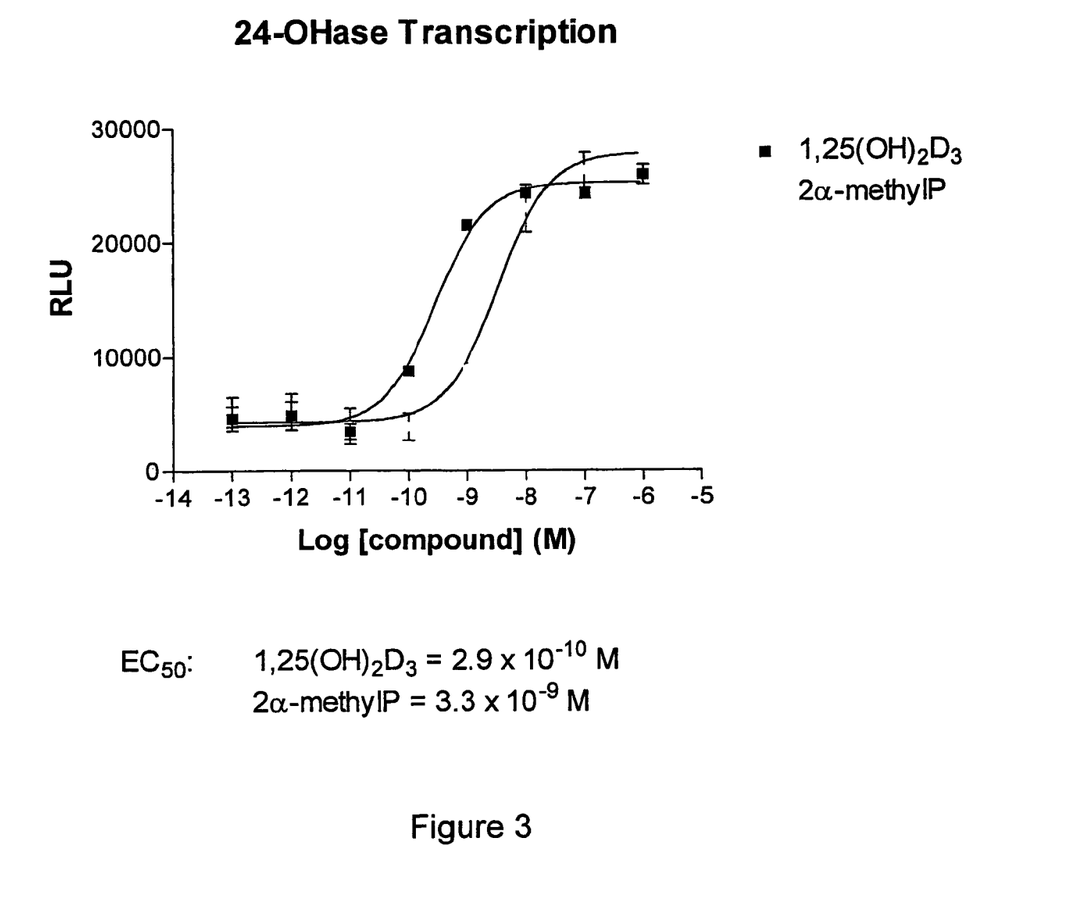
FIG. 3 is a graph illustrating the in vitro transcription activity of 1,25(OH)$_2D_3$ as compared to 2α-methylP.

FIG. 3 illustrates that the compound 2α-methylP has similar transcriptional activity as 1α,25-dihydroxyvitamin $D_3$ in bone cells. This result, together with the cell differentiation activity of FIG. 2, suggests that 2α-methylP will be very effective in psoriasis because it has direct cellular activity in causing cell differentiation, gene transcription and in suppressing cell growth. These data also indicate that 2α-methylP may have significant activity as an anti-cancer agent, especially against leukemia, colon cancer, breast cancer, skin cancer and prostate cancer.

Figure 6:
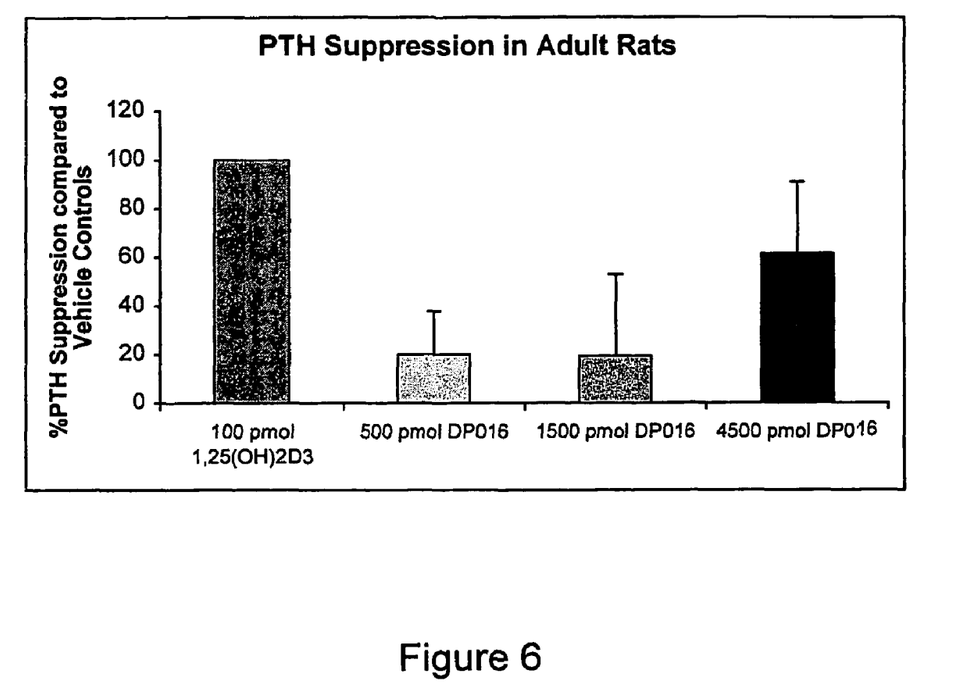
FIG. 6 is a bar graph illustrating the % PTH suppression of 1,25(OH)$_2D_3$ and 2α-methylP as compared to vehicle controls.

FIG. 6 illustrates that 2α-methyl P has the ability to suppress expression of parathyroid hormone (PTH), although not as potently as 1,25$(OH)_2D_3$.

The strong activity of 2α-methylP on HL-60 differentiation suggests it will be active in suppressing growth of parathyroid glands and in the suppression of the preproparathyroid gene.

Experimental Methods

Vitamin D Receptor Binding
Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25 $(OH)_2D_3$: molar extinction coefficient=18,200 and $\lambda_{max}$=265 nm; Analogs: molar extinction coefficient=42,000 and $\lambda_{max}$=252 nm). Radiolabeled ligand (3H-1,25$(OH)_2D_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation
Test Material
Study Drugs

The study drugs were dissolved in ethanol and the concentrations determined using UV spectrophotometry. Serial dilutions were prepared so that a range of drug concentrations could be tested without changing the final concentration of ethanol ($\leq 0.2\%$) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (0.47% Ca) diet+AEK for one week followed by Diet 11 (0.02% Ca)+AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

PTH Suppression and Hypercalcemia
Species

Adult, female Sprague-Dawley rats were obtained from Harlan (Madison, Wis.).

Animal Husbandry

Upon receipt, the animals were identified by individual tail marks. Animals were housed in suspended, stainless steel, wire-bottom cages. Each cage contained one animal. The animal rooms were maintained at a temperature of 68 to 72° F. and a relative humidity of 25 to 75%. The holding rooms were set to provide 12 hours of light per day.

Water and a purified rodent diet (Suda et al., Purified Rodent Diet-Diet 11) containing 0.47% and 0.3% phosphorus and fat soluble vitamins A, D, E and K were provided ad libitum.

Treatment Groups

Animals were randomly assigned to treatment groups (5 animals/group). All doses were administered intraperitoneally in 100 microliters of propylene glycol. Four to seven consecutive doses were given approximately 24 hours apart. Dosing was initiated after the animals had been allowed to acclimate for at least one week.

Dose Preparation
Control Material
Negative Control Material

The negative control material was prepared by volumetrically measuring ethanol (<5%) and propylene glycol, mixing and then placing in storage at 2 to 8° C.

Positive Control Material $1,25(OH)_2D_3$ was prepared by determining the concentration of an ethanol stock solution using UV spectrophotometry (extinction coefficient=18,200; $\lambda_{max}$=265 nm). The required amount of $1,25(OH)_2D_3$ was volumetrically measured into propylene glycol so that there was less than 5% ethanol in the final solution. The solution was mixed and then stored at 2 to 8° C.

Test Material

The analogs were prepared by first determining the concentration of an ethanol stock solution using UV spectrophotometry (extinction coefficient=42,000; $\lambda_{max}$=252 nm). The analog solutions were then volumetrically added to propylene glycol so that there was less than 5% ethanol in the final solution. The solution was mixed and stored at 2 to 8° C.

Dose Administration Method

Both control and test articles were administered by intraperitoneal injection in 100 microliters for 4-7 consecutive days spaced approximately 24 hours apart. $1,25(OH)_2D_3$ was given for 4 consecutive days, whereas, the test drugs were given for 7 consecutive days.

Serum PTH Levels.

Twenty-four hours after the final dose, blood was collected from the tail artery and the concentration of bioactive serum PTH was measured using the rat BioActive Intact PTH ELISA Kit from Immutopics, Inc. (San Clemente, Calif.).

Serum Calcium Analysis

Twenty-four hours after the final dose, approximately 1 ml of blood was collected from the tail artery of each experimental animal. The blood was allowed to coagulate at room temperature and then centrifuged at 3000×g for 15 minutes. The serum was transferred to a polypropylene tube and stored frozen at −20° C. The level of calcium was determined by diluting the serum into 0.1% lanthum chloride and measuring the absorbance on an atomic absorption spectrophotometer (Perkin Elmer Model 3110, Shelton, Conn.).

Interpretation of Data

VDR bindings HL60 cell differentiation, and transcription activity. 2α-methylP ($K_i$=9.4×10$^{-10}$M) is slightly less than the natural hormone 1α,25-dihydroxyvitamin $D_3$ ($K_i$=1.3×10$^{-10}$M) in its ability to compete with [$^3$H]-1,25(OH)$_2$D$_3$ for binding to the full-length recombinant rat vitamin D receptor (FIG. 1). There is also little difference between 2α-methylP ($EC_{50}$=3.8×10$^{-8}$ M) in its ability (efficacy or potency) to promote HL60 differentiation as compared to 1α,25-dihydroxyvitamin $D_3$ ($EC_{50}$=3.6×10$^{-9}$ M) (See FIG. 2). Also, compound 2α-methylP ($EC_{50}$=3.3×10$^{-9}$ M) has similar transcriptional activity in bone cells as 1α,25-dihydroxyvitamin $D_3$ ($EC_{50}$=2.9×10$^{-10}$ M) (See FIG. 3). These results suggest that 2α-methylP will be very effective in psoriasis because it has direct cellular activity in causing cell differentiation, gene transcription, and in suppressing cell growth. These data also indicate that 2α-methylP will have significant activity as an anti-cancer agent, especially against leukemia, colon cancer, breast cancer, skin cancer and prostate cancer, as well as against skin conditions such as dry skin (lack of dermal hydration), undue skin slackness (insufficient skin firmness), insufficient sebum secretion and wrinkles. It would also be expected to be very active in suppressing secondary hyperparathyroidism.

Calcium mobilization from bone and intestinal calcium absorption in vitamin D-deficient animals. Using vitamin D-deficient rats on a low calcium diet (0.02%), the activities of 2α-methylP and 1,25(OH)$_2$D$_3$ in intestine and bone were tested. As expected, the native hormone (1,25(OH)$_2$D$_3$) increased serum calcium levels at all dosages (FIG. 4). FIG. 4 shows that 2α-methylP has little, if any, activity in mobilizing calcium from bone. Administration of 2α-methylP at 87 pmol/day for 4 consecutive days did not result in mobilization of bone calcium, and increasing the amount of 2α-methylP to 260 pmol/day and then to 780 pmol/day and finally to 2340 pmol/day was also without any substantial effect.

Intestinal calcium transport was evaluated in the same groups of animals using the everted gut sac method (FIG. 5). These results show that the compound 2α-methylP does not promote intestinal calcium transport when administered at 87 pmol/day, 260 pmol/day, 780 pmol/day, or 2340 pmol/day, whereas 1,25(OH)$_2$D$_3$ promotes a significant increase at the 260 pmol/day dose. Thus, it may be concluded that 2α-methylP is essentially devoid of intestinal calcium transport activity at the tested doses.

PTH Suppression. The activities of 2α-methylP and 1,25 (OH)$_2$D$_3$ in PTH suppression were also tested. As expected, 1,25(OH)$_2$D$_3$ caused 100% PTH suppression when administered at 100 pmol/day. FIG. 6 also shows that 2α-methyl P suppresses PTH although it is not as effective as 1,25(OH)$_2$D$_3$ in this regard. Administration of 2α-methyl P at 500 pmol/day and at 1500 pmol/day resulted in about 20% PTH suppression whereas administration of 4500 pmol/day resulted in about 60% PTH suppression. These results together with the data in FIGS. 4 and 5 suggest that 2α-methylP will be very effective in treating secondary hyperparathyroidism of renal osteodystrophy because it has the ability to suppress PTH without raising blood calcium levels.

These results illustrate that 2α-methylP is an excellent candidate for numerous human therapies as described herein, and that it may be particularly useful in a number of circumstances such as suppression of secondary hyperparathyroidism of renal osteodystrophy, autoimmune diseases, cancer, and psoriasis. 2α-methylP is an excellent candidate for treating psoriasis because: (1) it has significant VDR binding, transcription activity and cellular differentiation activity; (2) it is devoid of hypercalcemic liability unlike 1,25(OH)$_2$D$_3$; and (3) it is easily synthesized. Since 2α-methylP has significant binding activity to the vitamin D receptor and suppresses PTH expression, but has little ability to raise blood serum calcium, it may also be particularly useful for the treatment of secondary hyperparathyroidism of renal osteodystrophy.

These data also indicate that the compound 2α-methylP of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound 2α-methylP of the invention.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly 2α-methylP, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 μg to 1000 μg per day of the compounds I, particularly 2α-methylP, preferably from about 0.1 μg to about 500 μg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin D$_2$ or D$_3$, or 1α,25-dihydroxyvitamin D$_3$—in situations where different degrees of bone mineral mobilization and calcium transport stimulation is found to be advantageous.

Compositions for use in the above-mentioned treatments comprise an effective amount of the compounds I, particularly 2α-methylP, as defined by the above formula I and Ia as the active ingredient, and a suitable carrier. An effective amount of such compound for use in accordance with this invention is from about 0.01 μg to about 1000 μg per gm of composition, preferably from about 0.1 μg to about 500 μg per gram of composition, and may be administered topically, transdermally, orally, rectally, nasally, sublingually or parenterally in dosages of from about 0.01 μg/day to about 1000 μg/day, and preferably from about 0.1 μg/day to about 500 μg/day.

The compounds I, particularly 2α-methylP, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly 2α-methylP, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound having the formula:

where $X_1$ and $X_2$, which may be the same or different, are each selected from hydrogen or a hydroxy-protecting group.

2. The compound of claim 1 wherein $X_2$ is hydrogen.

3. The compound of claim 1 wherein $X_1$ is hydrogen.

4. The compound of claim 1 wherein $X_1$ and $X_2$ are both t-butyldimethylsilyl.

5. A pharmaceutical composition containing an effective amount of at least one compound as claimed in claim 1 together with a pharmaceutically acceptable excipient.

6. The pharmaceutical composition of claim 5 wherein said effective amount comprises from about 0.01 μg to about 1000 μg per gram of composition.

7. The pharmaceutical composition of claim 5 wherein said effective amount comprises from about 0.1 μg to about 500 μg per gram of composition.

8. 2α-methyl-19-nor-1α-hydroxy-homopregnacalciferol having the formula:

9. A pharmaceutical composition containing an effective amount of 2α-methyl-19-nor-1α-hydroxy-homopregnacalciferol together with a pharmaceutically acceptable excipient.

10. The pharmaceutical composition of claim 9 wherein said effective amount comprises from about 0.01 μg to about 1000 μg per gram of composition.

11. The pharmaceutical composition of claim 9 wherein said effective amount comprises from about 0.1 μg to about 500 μg per gram of composition.

12. A method of treating psoriasis comprising administering to a subject with psoriasis an effective amount of a compound having the formula:

where $X_1$ and $X_2$, which may be the same or different, are each selected from hydrogen or a hydroxy-protecting group.

13. The method of claim 12 wherein the compound is administered orally.

14. The method of claim 12 wherein the compound is administered parenterally.

15. The method of claim 12 wherein the compound is administered transdermally.

16. The method of claim 12 wherein the compound is administered topically.

17. The method of claim 12 wherein the compound is administered rectally.

18. The method of claim 12 wherein the compound is administered nasally.

19. The method of claim 12 wherein the compound is administered sublingually.

20. The method of claim 12 wherein the compound is administered in a dosage of from about 0.01 μg/day to about 1000 μg/day.

21. The method of claim 12 wherein the compound is 2α-methyl-19-nor-1α-hydroxy-homopregnacalciferol having the formula:

22. A method of treating a disease selected from the group consisting of leukemia, colon cancer, breast cancer, skin cancer or prostate cancer comprising administering to a subject with said disease an effective amount of a compound having the formula:

where $X_1$ and $X_2$, which may be the same or different, are each selected from hydrogen or a hydroxy-protecting group.

23. The method of claim 22 wherein the compound is administered orally.

24. The method of claim 22 wherein the compound is administered parenterally.

25. The method of claim 22 wherein the compound is administered transdermally.

26. The method of claim 22 wherein the compound is administered rectally.

27. The method of claim 22 wherein the compound is administered nasally.

28. The method of claim 22 wherein the compound is administered sublingually.

29. The method of claim 22 wherein the compound is administered in a dosage of from about 0.01 μg/day to about 1000 μg/day.

30. The method of claim 22 wherein the compound is 2α-methyl-19-nor-1α-hydroxy-homopregnacalciferol having the formula:

31. A method of treating an autoimmune disease selected from the group consisting of multiple sclerosis, lupus, diabetes mellitus, host versus graft rejection, and rejection of organ transplants, comprising administering to a subject with said disease an effective amount of a compound having the formula:

where $X_1$ and $X_2$, which may be the same or different, are each selected from hydrogen or a hydroxy-protecting group.

32. The method of claim 31 wherein the compound is administered orally.

33. The method of claim 31 wherein the compound is administered parenterally.

34. The method of claim 31 wherein the compound is administered transdermally.

35. The method of claim 31 wherein the compound is administered rectally.

36. The method of claim 31 wherein the compound is administered nasally.

37. The method of claim 31 wherein the compound is administered sublingually.

38. The method of claim 31 wherein the compound is administered in a dosage of from about 0.01 μg/day to about 1000 μg/day.

39. The method of claim 31 wherein the compound is 2α-methyl-19-nor-1α-hydroxy-homopregnacalciferol having the formula:

40. A method of treating an inflammatory disease selected from the group consisting of rheumatoid arthritis, asthma, and inflammatory bowel diseases, comprising administering to a subject with said disease an effective amount of a compound having the formula:

where $X_1$ and $X_2$, which may be the same or different, are each selected from hydrogen or a hydroxy-protecting group.

41. The method of claim 40 wherein the compound is administered orally.

42. The method of claim 40 wherein the compound is administered parenterally.

43. The method of claim 40 wherein the compound is administered transdermally.

44. The method of claim 40 wherein the compound is administered rectally.

45. The method of claim 40 wherein the compound is administered nasally.

46. The method of claim 40 wherein the compound is administered sublingually.

47. The method of claim 40 wherein the compound is administered in a dosage of from about 0.01 μg/day to about 1000 μg/day.

48. The method of claim 40 wherein the compound is 2α-methyl-19-nor-1α-hydroxy-homopregnacalciferol having the formula:

49. A method of treating a skin condition selected from the group consisting of wrinkles, lack of adequate skin firmness, lack of adequate dermal hydration and insufficient sebum secretion which comprises administering to a subject with said skin condition an effective amount of a compound having the formula:

where $X_1$ and $X_2$, which may be the same or different, are each selected from hydrogen or a hydroxy-protecting group.

50. The method of claim 49 wherein the compound is administered orally.

51. The method of claim 49 wherein the compound is administered parenterally.

52. The method of claim 49 wherein the compound is administered transdermally.

53. The method of claim 49 wherein the compound is administered topically.

54. The method of claim 49 wherein the compound is administered rectally.

55. The method of claim 49 wherein the compound is administered nasally.

56. The method of claim 49 wherein the compound is administered sublingually.

57. The method of claim 49 wherein the compound is administered in a dosage of from about 0.01 µg/day to about 1000 µg/day.

58. The method of claim 49 wherein the compound is 2α-methyl-19-nor-1α-hydroxy-homopregnacalciferol having the formula:

59. A method of treating renal osteodystrophy comprising administering to a subject with renal osteodystrophy an effective amount of a compound having the formula:

where $X_1$ and $X_2$, which may be the same or different, are each selected from hydrogen or a hydroxy-protecting group.

60. The method of claim 59 wherein the compound is administered orally.

61. The method of claim 59 wherein the compound is administered parenterally.

62. The method of claim 59 wherein the compound is administered transdermally.

63. The method of claim 59 wherein the compound is administered rectally.

64. The method of claim 59 wherein the compound is administered nasally.

65. The method of claim 59 wherein the compound is administered sublingually.

66. The method of claim 59 wherein the compound is administered in a dosage of from about 0.01 µg/day to about 1000 µg/day.

67. The method of claim 59 wherein the compound is 2α-methyl-19-nor-1α-hydroxy-homopregnacalciferol having the formula:

\* \* \* \* \*